(12) United States Patent
Mertoglu et al.

(10) Patent No.: US 9,374,996 B2
(45) Date of Patent: Jun. 28, 2016

(54) AGROFORMULATION COMPRISING COPOLYMER OF ACRYLIC ACID, POLY(ALKYLENE GLYCOL) (METH)ACRYLATE, AND ALKYL (METH)ACRYLATE

(71) Applicant: BASF SE, Ludwigshafen (DE)

(72) Inventors: Murat Mertoglu, Ludwigshafen (DE); Ann-Kathrin Marguerre, Heidelberg (DE); Vandana Kurkal-Siebert, Heidelberg (DE); Son Nguyen-Kim, Hemsbach (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/391,925

(22) PCT Filed: Mar. 22, 2013

(86) PCT No.: PCT/EP2013/056074
§ 371 (c)(1),
(2) Date: Oct. 10, 2014

(87) PCT Pub. No.: WO2013/156249
PCT Pub. Date: Oct. 24, 2013

(65) Prior Publication Data
US 2015/0126363 A1    May 7, 2015

Related U.S. Application Data

(60) Provisional application No. 61/624,419, filed on Apr. 16, 2012.

(30) Foreign Application Priority Data

Apr. 16, 2012  (EP) ..................... 12164254

(51) Int. Cl.
| | | |
|---|---|---|
| *A01N 25/02* | (2006.01) |
| *A01N 25/30* | (2006.01) |
| *A01N 43/653* | (2006.01) |
| *A01N 43/40* | (2006.01) |
| *A01N 43/56* | (2006.01) |

(52) U.S. Cl.
CPC ............... *A01N 25/02* (2013.01); *A01N 25/30* (2013.01); *A01N 43/40* (2013.01); *A01N 43/56* (2013.01); *A01N 43/653* (2013.01)

(58) Field of Classification Search
CPC ....................................................... A01N 25/02
See application file for complete search history.

(56) References Cited

U.S. PATENT DOCUMENTS

| | | |
|---|---|---|
| 2011/0039704 A1 | 2/2011 | Sixl et al. |
| 2011/0082039 A1 | 4/2011 | Keeney et al. |

FOREIGN PATENT DOCUMENTS

| | | |
|---|---|---|
| WO | WO 95/07614 | 3/1995 |
| WO | WO 2008/091746 | 7/2008 |
| WO | WO 2009/073164 | 6/2009 |
| WO | WO 2011/018188 | 2/2011 |
| WO | WO 2013149856 | 10/2013 |
| WO | WO 2013149925 | 10/2013 |

OTHER PUBLICATIONS

International Search Report, PCT/EP2013/056074, filed Mar. 22, 2013, search completed Apr. 25, 2013.
International Preliminary Report on Patentability, PCT/EP2013/056074, filed Mar. 22, 2013, report completed Apr. 1, 2014.

*Primary Examiner* — Carlos Azpuru
(74) *Attorney, Agent, or Firm* — Brinks Gilson & Lione

(57) ABSTRACT

The present invention provides a composition comprising a pesticide and a copolymer, which contains in polymerized form acrylic acid and/or methacrylic acid (monomer A); a mono $C_{12}$-$C_{22}$ alkyl terminated poly($C_{2\text{-}6}$ alkylene glycol) (meth)acrylate (monomer B); and a $C_1$-$C_8$ alkyl(meth)acrylate (monomer C). Further on, it provides a process for preparing said composition by contacting the pesticide and the copolymer; a method for controlling phytopathogenic fungi and/or unwanted plant growth and/or unwanted insect or mite infestation and/or for regulating the growth of plants, wherein said composition is caused to act on the respective pests, their habitat or the plants to be protected from the respective pest, to the soil and/or to unwanted plants and/or the crop plants and/or their habitat; and a plant propagation material comprising said composition.

12 Claims, No Drawings

AGROFORMULATION COMPRISING COPOLYMER OF ACRYLIC ACID, POLY(ALKYLENE GLYCOL) (METH)ACRYLATE, AND ALKYL (METH)ACRYLATE

This application is a National Stage application of International Application No. PCT/EP2013/056074, filed Mar. 22, 2013, which claims the benefit of U.S. Provisional Application No. 61/624,419, filed Apr. 16, 2012, the entire contents of which are hereby incorporated herein by reference. This application also claims priority under 35 U.S.C. §119 to EP Patent Application No. 12164254.0, filed Apr. 16, 2012, the entire contents of which is hereby incorporated herein by reference.

The present invention provides a composition comprising a pesticide and a copolymer, which contains in polymerized form acrylic acid and/or methacrylic acid (monomer A); a mono $C_1$-$C_{22}$ alkyl terminated poly($C_{2-6}$ alkylene glycol) (meth)acrylate (monomer B); and a $C_1$-$C_8$ alkyl(meth)acrylate (monomer C). Further on, it provides a process for preparing said composition by contacting the pesticide and the copolymer; a method for controlling phytopathogenic fungi and/or unwanted plant growth and/or unwanted insect or mite infestation and/or for regulating the growth of plants, wherein said composition is caused to act on the respective pests, their habitat or the plants to be protected from the respective pest, to the soil and/or to unwanted plants and/or the crop plants and/or their habitat; and a plant propagation material comprising said composition. Combinations of preferred features with other preferred features are encompassed by the present invention.

Stabilizing pesticides, in particular water-insoluble ones, in agrochemical formulations is difficult. In liquid formulations in particular, the pesticides tend to crystallize, especially at low temperatures. It is also hard to formulate high concentrations of water-insoluble pesticides. Often times the required crystallization inhibitors are soluble in the formulations only at low concentrations. It was an object of the present invention to resolve these drawbacks.

The object has been achieved by means of a composition comprising a pesticide and a copolymer, which contains in polymerized form
acrylic acid and/or methacrylic acid (monomer A);
a mono $C_{12}$-$C_{22}$ alkyl terminated poly($C_{2-6}$ alkylene glycol) (meth)acrylate (monomer B); and
a $C_1$-$C_8$ alkyl(meth)acrylate (monomer C).

Suitable monomers A are acrylic acid, methacrylic acid, and mixtures thereof. Preferred monomer A is methacrylic acid.

Suitable monomers B are mono $C_{12-22}$ alkyl terminated poly($C_{2-6}$ alkylene glycol)(meth)acrylate. Preferred monomer B are mono $C_{14-20}$ alkyl terminated poly($C_{2-4}$ alkylene glycol)(meth)acrylate. More preferred monomer B are mono $C_{12-22}$ alkyl terminated poly(ethylene glycol)(meth)acrylate. Especially preferred monomer B are mono $C_{14-20}$ alkyl terminated poly(ethylene glycol)(meth)acrylate. The monomer B comprises usually 2 to 60 units, preferably 3 to 35 units of the alkylene glycol (e.g. ethylen glycol).

Suitable $C_1$-$C_8$-alkyl(meth)acrylates (monomer C) are acrylic and methacrylic acid esters of $C_1$-$C_8$-alkanols, such as methyl acrylate, ethyl acrylate, n-butyl acrylate, tert-butyl acrylate, methyl methacrylate, ethyl methacrylate, n-butyl methacrylate, tert-butyl methacrylate, n-hexyl(meth)acrylate, branched octyl(meth)acrylate, and mixtures thereof. Preferred monomer C are (meth)acrylates, and in particular methyl methacrylate.

The copolymer may contain further monomers (monomer D). Suitable are any monomers which are polymerizable with monomers A, B and C, such as ethylenically unsaturated monomers. In another form, the copolymer contains less than 5 wt %, preferably less than 2 wt %, and in particular no monomer D, which comprise a sulfonic acid group, such as 2-acrylamido-2-methylpropanesulfonic acid (AMPS).

Preferably, the copolymer is soluble in organic solvents (e.g. N,N-dimethyldodecanamide) at 20° C. at a concentration of 10 g/l, preferably even at 50 g/l. The copolymer is preferably present in dissolved form in the composition.

The copolymer may contain at least 1 wt %, preferably at least 5 wt %, and in particular at least 8 wt % monomer A, based on the total amount of monomers. The copolymer may contain up to 50 wt %, preferably up to 35 wt %, and in particular up to 25 wt % monomer A, based on the total amount of monomers.

The copolymer may contain at least 5 wt %, preferably at least 20 wt %, and in particular at least 25 wt % monomer B, based on the total amount of monomers. The copolymer may contain up to 60 wt %, preferably up to 50 wt %, and in particular up to 40 wt % monomer B, based on the total amount of monomers.

The copolymer may contain at least 15 wt %, preferably at least 30 wt %, and in particular at least 40 wt % monomer C, based on the total amount of monomers. The copolymer may contain up to 85 wt %, preferably up to 80 wt %, and in particular up to 70 wt % monomer C, based on the total amount of monomers.

The copolymer may contain up to 15 wt %, preferably up to 10 wt %, and in particular up to 2 wt % monomer D, based on the total amount of monomers. In another form the copolymer is essentially free of monomer D.

Usually, the sum of monomers A, B, C and D equals 100%.

The sum of monomers B and C is usually at least 40 wt %, preferably at least 50 wt %, and in particular at least 60 wt %, based on the total amount of monomers.

The copolymer may contain at least 5 wt % monomer A, at least 20 wt % monomer B, at least 30 wt % monomer C, wherein the sum of monomers B and C is at least 50 wt %, based on the total amount of monomers.

The copolymer may contain
3 to 40 wt % monomer A,
10 to 45 wt % monomer B,
20 to 80 wt % monomer C, and
up to 15 wt % further monomers D,
wherein the sum of monomers A, B, C and D equals 100%.

Preferably, the copolymer contains
5 to 30 wt % monomer A,
20 to 40 wt % monomer B,
30 to 70 wt % monomer C, and
up to 10 wt % further monomers D,
wherein the sum of monomers A, B, C and D equals 100%.

The copolymers generally have an average molar weight Mw in the range from 1000 to 100 000 g/mol, preferably 2000 to 50 000 g/mol, more preferably 2000 to 30 000 g/mol. The average molar weight MN is generally in the range from 1000 to 50 000 g/mol, preferably 1000 to 15 000 g/mol, more particularly 2000 to 8000 g/mol.

The proportion of the monomers A-D in the copolymer is usually at least 85% by weight, preferably at least 90% by weight, more particularly at least 95% by weight, and especially at least 98% by weight. The copolymer may optionally comprise free-radical initiator molecules and additional regulators or chain-transfer agents.

The copolymers are obtainable by usual polymerization processes, such as solution polymerization.

The copolymer is preferably obtainable by free-radical polymerization of the monomers A-D either (i) in a solvent mixture composed of water and at least one organic solvent having a boiling point<140° C. or (ii) in one or more pure alcohols. The typical processes of free or controlled, preferably free, radical polymerization may be used, the reaction mixture comprising at least one initiator. The solvent mixture is preferably selected such that the monomers and also the copolymer formed are soluble. Soluble here, in the sense of the invention, encompasses not only a true solution but also a dispersion which is so finely divided that there is no clouding produced. The polymerization may be carried out as a batch reaction, in a semibatch procedure or in a continuous procedure. The polymerization is usually carried out in solution.

Suitable organic solvents for polymerization include in principle all solvents having a boiling point of less than 140° C. Preferred solvents are those which are miscible with water and have a boiling point≤120° C. Particularly preferred organic solvents are alcohols, ethers, and nitriles. Examples of particularly preferred alcohols include methanol, ethanol, n-propanol (1-propanol), isopropanol (2-propanol), n-butanol (1-butanol), sec-butanol (2-butanol), tert-butanol (2-methylpropan-2-ol), 1-pentanol, 2-pentanol, 3-pentanol, 2-methylbutanol, 3-methylbutan-2-ol and 2,2-dimethylpropanol. Especially preferred alcohols are methanol, ethanol, n-propanol (1-propanol), and isopropanol (2-propanol). More particular preference is given to isopropanol (2-propanol).

The reaction times are situated generally in the range between 1 and 48 h, preferably in the range from 2 to 24 h, and with more particular preference in the range from 4 to 24 h. The temperature range within which the reaction can be carried out extends generally from 20 to 200° C., preferably from 30 to 120° C., and with more particular preference from 40 to 90° C.

As initiators for the free-radical polymerization, typical radical-forming substances are used. The initiator is selected preferably from the group of the azo compounds, the peroxide compounds or the hydroperoxide compounds. Examples include acetyl peroxide, benzoyl peroxide, lauroyl peroxide, tert-butyl peroxyisobutyrate, caproyl peroxide, cumene hydroperoxide, azobis(isobutyronitrile), 2,2-azobis(2-methylbutyronitrile), 2,2'-azobis(2-methylpropionamidine)dihydrochloride, and 2,2'-azobis[2-(2-imidazolin-2-yl)propane] dihydrochloride. It will be appreciated that initiator mixtures can also be used.

The polydispersity and the molecular weight of the random free-radical copolymer may be adjusted if desired through the variation of the initiator/monomer ratio, the feed time of the substrates, especially the feed time of the initiator solution in comparison to the feed time of the monomer solution(s), through variation in the alcohol content, more particularly isopropanol content, of the solvent mixture, and through the polymerization concentration. If a short initiator feed and/or a high isopropanol content (regulator or chain-transfer agent) in the solvent mixture is selected, and/or if a low polymerization concentration (high regulator/monomer ratio) is selected, the resulting polydispersities are generally relatively low. Through the use of additional regulators or chain-transfer agents from the group of the mecaptans, such as mercaptoethanol, thioglycerol or 1-dodecyl mercaptan, it is possible, if desired, to achieve a further reduction in the polydispersity of the copolymer. The molar masses Mw and Mn and also the polydispersity are determined by means of size exclusion chromatography. Calibrating agents that can be used are commercial polystyrene or poly(ethylene oxide) calibration sets.

The copolymer may if desired be isolated and worked up. Workup is accomplished in a known way familiar to the skilled person, as for example by a prior filtration step. This makes it possible optionally to remove the 2-amino-2-methylpropanesulfonic acid byproduct. If desired, the solvent may subsequently be removed. Examples of typical methods of removing the solvent include spray drying, evaporation at reduced pressure, freeze drying, and evaporation under atmospheric pressure with optionally elevated temperature. The methods suitable for drying further include drying in a fluidized bed dryer. Another option is to use the copolymer solution obtainable by the process without workup.

The term pesticides identifies at least one active ingredient selected from the group of fungicides, insecticides, nematicides, herbicides, safeners and/or growth regulators. Preferred pesticides are fungicides, insecticides, herbicides, and growth regulators. Particularly preferred pesticides are fungicides. Mixtures of pesticides from two or more of the aforementioned classes may also be used. The skilled person is familiar with such pesticides, which may be found in, for example, Pesticide Manual, 15th Ed. (2009), The British Crop Protection Council, London. Suitable insecticides are insecticides from the classes of the carbamates, organophosphates, organochlorine insecticides, phenylpyrazoles, pyrethroids, neonicotinoids, spinosins, avermectins, milbemycins, juvenile hormone analogs, alkyl halides, organotin compounds, nereistoxin analogs, benzoylureas, diacylhydrazines, METI acaricides, and also insecticides such as chloropicrin, pymetrozine, flonicamide, clofentezine, hexythiazox, etoxazole, diafenthiuron, propargite, tetradifon, chlorfenapyr, DNOC, buprofezine, cyromazine, amitraz, hydramethylnon, acequinocyl, fluacrypyrim, rotenone, or derivatives thereof. Suitable fungicides are fungicides from the classes of the dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzylcarbamates, carbamates, carboxamides, carboxylic amides, chloronitriles, cyanoacetamide oximes, cyanoimidazoles, cyclopropanecarboxamides, dicarboximides, dihydrodioxazines, dinitrophenylcrotonates, dithiocarbamates, dithiolanes, ethylphosphonates, ethylaminothiazolecarboxamides, guanidines, hydroxy(2-amino)-pyrimidines, hydroxyanilides, imidazoles, imidazolinones, inorganics, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, and triazoles. Suitable herbicides are herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ethers, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl (thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, and ureas.

Preferred pesticides are water-insoluble pesticides. Water-insoluble pesticides may have a solubility in water of up to and including 10 g/l at 20° C. Their solubility in water is preferably not more than 1 g/l, more preferably not more than 0.5 g/l. Examples of suitable water-insoluble pesticides (solubility in water at 20° C. in each case in parentheses) are pyraclostrobin (1.9 mg/l), epoxiconazole (7 mg/l), prochloraz (34 mg/l), metconazole (30 mg/l), fluxapyroxad (0.00388 g/l) and/or fenpropimorph (4 mg/l).

The pesticide (e.g. the water-insoluble pesticide) usually has a melting point of at least 30° C., preferably of at least 50° C., more preferably of at least 70° C., and very preferably of at least 100° C.

The pesticide (e.g. the water-insoluble pesticide) is preferably present in dissolved form in the composition. This means that typically at least 90% by weight, preferably at least 99% by weight, of the water-insoluble pesticide is in dissolved form.

Besides the pesticide, the composition may also comprise further pesticides. The further pesticide may be present in dissolved form or in the form of solid particles (e.g., in suspension). The composition may comprise at least one organic solvent, as for example one, two, three or four different solvents. The composition preferably comprises at least two organic solvents.

Organic solvents contemplated include solvents such as mineral oil fractions of medium to high boiling point such as kerosene and diesel oil, and also coal tar oils, and also oils of plant or animal origin, aliphatic, cyclic, and aromatic hydrocarbons, e.g., paraffins, tetrahydronaphthalene, alkylated naphthalenes and derivatives thereof, alkylated benzenes and derivatives thereof, alcohols such as methanol, ethanol, propanol, butanol, and cyclohexanol, glycols, ketones such as cyclohexanone and gamma-butyrolactone, dimethyl fatty acid amides, alkylene carbonates, fatty acids, DMSO, alkyl alkanoates; or N-methylpyrrolidone. In principle it is also possible to use solvent mixtures.

At least one organic solvent may have a solubility in water at 20° C. of not more than 10% by weight, preferably not more than 8% by weight, more preferably not more than 6% by weight, and especially not more than 3% by weight.

Preferred organic solvents comprise at least one amide of the formula (I)

$$R^1\text{—C(O)N(R}^2)_2 \tag{I}$$

where $R^1$ is $C_5$-$C_{19}$-alkyl, and $R^2$ is $C_1$-$C_4$-alkyl. Preferred amides of the formula (I) are those, where $R^1$ is $C_7$-$C_{14}$-alkyl, and $R^2$ is methyl. Especially preferred amides of the formula (I) are those, where $R^1$ is $C_7$-$C_{12}$-alkyl, and $R^2$ is methyl. Mixtures of said amides are also possible.

The organic solvent may comprise at least one amide of the formula (I) and a further solvent selected from an alkyl alkanoate and an hydrocarbon oil.

Suitable hydrocarbon oils contain aliphatic, cycloaliphatic and aromatic hydrocarbons, e.g. toluene, paraffin, tetrahydronaphthalene, alkylated naphthalenes. Also suitable are mineral oil fractions of medium to high boiling point, e.g. kerosene, diesel oil. Also suitable are alkyl-substituted aromatics, such as toluene, the xylenes, ethylbenzenes and benzenes with relatively long-chain alkyl radicals, e.g. $C_9$-$C_{10}$-dialkyl- and trialkylbenzenes (e.g. available under the name Solvesso® 100 from Exxon Mobile Europe or Aromatic 100 from Exxon Mobile USA), $C_{10}$-$C_{11}$-alkylbenzenes (e.g. available under the name Solvesso® 150 from Exxon Mobile Europe or Aromatic 150 from Exxon Mobile USA) and alkylnaphthalenes (e.g. available under the name Solvesso® 200 from Exxon Mobile Europe or Aromatic 200 from Exxon Mobile USA). Preferably, the hydrocarbon oil contains at least 50 wt %, more preferably at least 85 wt %, and in particular at least 95 wt % aliphatic and/or cycloaliphatic hydrocarbons. In another preferred form, the hydrocarbon oil contains up to 10 wt %, preferably up to 5 wt %, and in particular up to 3 wt % aromatic hydrocarbons. In another preferred form, the adjuvant contains up to 5 wt %, preferably up to 2.5 wt %, and in particular up to 1.5 wt % aromatic hydrocarbons.

Suitable alkyl alkanoates are fatty acid esters, diesters of diacids, esters of hydroxy acids. Preferred alkyl alkanoates are diesters of diacids (such as linear or branched di-$C_1$-$C_{20}$ alkyl esters of linear, branched or cyclic aliphatic $C_4$-$C_{18}$ diacids). More preferred alkyl alkanoates are linear or branched di-$C_1$-$C_6$ alkyl esters of linear aliphatic $C_4$-$C_8$ diacids, such as dibutyl adipate.

The composition may comprise a nonionic surfactant. Suitable nonionic surfactants are surfactants from the classes of the alkoxylates, block polymers, N alkylated fatty acid amides, amine oxides, esters or sugar-based surfactants. Examples of alkoxylates are compounds such as alcohols, alkylphenols, amines, amides, arylphenols, fatty acids or fatty acid esters that have been alkoxylated. For the alkoxylation it is possible to use ethylene oxide and/or propylene oxide, preferably ethylene oxide. Examples of N-alkylated fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose esters and glucose esters or alkylpolyglucosides. Suitable block polymers are block polymers of the A-B or A-B-A type, comprising blocks of polyethylene oxide and polypropylene oxide, or of the A-B-C type, comprising alkanol, polyethylene oxide, and polypropylene oxide. Preferred nonionic surfactants are surfactants from the classes of alkoxylates and block polymers, more particularly alkoxylates.

The composition preferably comprises at least 20% by weight, more preferably at least 30% by weight, very preferably at least 40% by weight, and especially at least 50% by weight of organic solvent. The composition may comprise up to 90% by weight, preferably up to 80% by weight, of organic solvent.

The composition comprises preferably not more than 10% by weight, more preferably not more than 8% by weight, very preferably not more than 5% by weight, and especially not more than 1% by weight of water.

The composition may comprise from 30 to 95 wt %, preferably from 40 to 90 wt %, and in particular from 50 to 85 wt % organic solvent, which contains at least one amide of the formula (I) and optionally a further solvent selected from alkyl alkanoate and hydrocarbon oil.

The weight ratio of the amide of the formula (I) to the further solvent selected from alkyl alkanoate and hydrocarbon oil may be in the range of from 15:1 to 1:2, preferably from 10:1 to 1:1, and in particular from 7:1 to 1.5:1.

The composition preferably comprises at least 3% by weight, more preferably at least 5% by weight, very preferably at least 8% by weight, and especially at least 10% by weight of the copolymer. The composition may comprise up to 30% by weight, preferably up to 20% by weight, of the copolymer.

The composition comprises preferably at least 1% by weight, more preferably at least 3% by weight, and very preferably at least 5% by weight of pesticide. The composition may comprise up to 50% by weight, preferably up to 30% by weight, and more preferably up to 20% by weight of pesticide.

The composition preferably comprises at least 3% by weight, more preferably at least 6% by weight, very preferably at least 9% by weight, and especially at least 15% by weight of nonionic surfactant. The composition can comprise up to 80% by weight, preferably up to 50% by weight, more preferably up to 25% by weight of nonionic surfactant.

The composition comprises preferably
a) at least 3% by weight of copolymer;
b) at least 20% by weight of organic solvent;
c) not more than 6% by weight of water;
d) at least 1% by weight of pesticide; and
e) at least 3% by weight of nonionic surfactant.

The composition comprises more preferably
a) 2-20% by weight of copolymer;
b) 40-95% by weight of organic solvent;
c) not more than 3 wt % by weight of water;
d) 1-25% by weight of the water-insoluble pesticide; and
e) 3-50% by weight of nonionic surfactant.

Usually, the amounts of all components present in the composition add up to 100 wt %.

The weight ratio of copolymer to pesticide can be situated in the range from 10:1 to 1:10, preferably from 5:1 to 1:5, more preferably from 2:1 to 1:2.

The composition is typically a liquid composition, as for example an organic solution.

The composition of the invention may comprise formulating assistants, in which case the choice of assistants is governed typically by the specific application form and/or active ingredient. Examples of suitable formulating assistants are solvents, surface-active compounds (such as surfactants, protective colloids, wetting agents, and adhesive agents), organic and inorganic thickeners, bactericides, optionally colorants, and adhesives (e.g., for seed treatment).

Surface-active compounds contemplated (adjuvants, wetters, stickers, dispersants or emulsifiers) include the alkali metal, alkaline earth metal, and ammonium salts of aromatic sulfonic acids, e.g., of ligno- (Borresperse® products, Borregaard, Norway), phenol-, naphthalene- (Morwet® products, Akzo Nobel, USA), and dibutylnaphthalene-sulfonic acid (Nekal® products, BASF, Germany), and also of fatty acids, alkylsulfonates and alkylarylsulfonates, alkyl, lauryl ether, and fatty alcohol sulfates, and also salts of sulfated hexa-, hepta- and octadecanols, and also of fatty alcohol glycol ethers, condensation products of sulfonated naphthalene and its derivatives with formaldehyde, condensation products of naphthalene or of naphtalenesulfonic acids with phenol and formaldehyde, polyoxyethyleneoctyl phenol ethers, ethoxylated isooctylphenol, octylphenol or nonylphenol, alkylphenyl and tributylphenyl polyglycol ethers, alkylaryl polyether alcohols, isotridecyl alcohol, fatty alcohol ethylene oxide condensates, ethoxylated castor oil, polyoxyethylene- or polyoxypropylene-alkyl ethers, lauryl alcohol polyglycol ether acetate, sorbitol esters, lignin-sulfite waste liquors, and also proteins, denatured proteins, polysaccharides (e.g., methylcellulose), hydrophobically modified starches, polyvinyl alcohol (Mowiol® products, Clariant, Switzerland), polycarboxylates (Sokalan® products, BASF, Germany), polyalkoxylates, polyvinylamine (Lupamin® products, BASF, Germany), polyethylenimine (Lupasol® products, BASF, Germany), polyvinylpyrrolidone, and copolymers thereof.

Suitable thickeners are compounds which give the formulation a modified rheology, i.e., a high viscosity in the state of rest and low viscosity in the state of movement. Examples are polysaccharides, proteins (such as casein or gelatin), synthetic polymers or inorganic layered minerals. Thickeners of these kinds are available commercially, examples being xanthan gum (Kelzan®, CP Kelco, USA), Rhodopol® 23 (Rhodia, France) or Veegum® (R.T. Vanderbilt, USA) or Attaclay® (Engelhard Corp., NJ, USA). The amount of thickener in the formulation is governed by the efficacy of the thickener. The skilled person will select an amount in order to obtain the desired viscosity of the formulation. The amount will usually be 0.01 to 10% by weight. Bactericides may be added to stabilize the composition. Examples of bactericides are those based on dichlorophen and benzyl alcohol hemiformal, and also on isothiazolinone derivatives such as alkylisothiazolinones and benzisothiazolinones (Acticide® MBS from Thor Chemie).

In one preferred embodiment the compositions of the invention are in the form of an agrochemical formulation. The composition is preferably in the form of an emulsifiable concentrate (EC) or an oil dispersion (OD).

The agrochemical formulation is usually diluted before application to prepare what is called a tank mix. Contemplated for dilution are mineral oil fractions of medium to high boiling point, such as kerosene or diesel oil, and also coal tar oils, and also oils of plant or animal origin, aliphatic, cyclic, and aromatic hydrocarbons, e.g., toluene, xylene, paraffin, tetrahydronaphthalene, alkylated naphthalenes or derivatives thereof, methanol, ethanol, propanol, butanol, cyclohexanol, cyclohexanone, isophorone, strongly polar solvents, e.g., dimethyl sulfoxide, N-methylpyrrolidone or water. It is preferred to use water.

The diluted composition is typically applied by spraying or fogging. The tank mix may be admixed with oils of various types, wetting agents, adjuvants, herbicides, bactericides, and/or fungicides immediately prior to application (tank mix). These additions may be admixed to the compositions of the invention in a weight ratio of 1:100 to 100:1, preferably 1:10 to 10:1. The pesticide concentration in a tank mix may be varied within relatively wide ranges. Generally speaking it is between 0.0001% and 10%, preferably between 0.01% and 1%. The application rates for use in crop protection vary according to the nature of the desired effect and are between 0.01 and 2.0 kg of active ingredient per ha.

The invention further provides a process for preparing the composition of the invention, by contacting the copolymer, the pesticide, and optionally the organic solvent and optionally the nonionic surfactant. The components can be contacted with one another by methods which are general knowledge, such as mixing, emulsifying or suspending.

The invention further provides a method for controlling phytopathogenic fungi and/or unwanted plant growth and/or unwanted insect or mite infestation and/or for regulating the growth of plants, where the composition of the invention is caused to act on the respective pests, their habitat or the plants to be protected from the respective pest, to the soil and/or to unwanted plants and/or the crop plants and/or their habitat. The invention additionally provides for the use of the composition of the invention for controlling phytopathogenic fungi and/or unwanted plant growth and/or unwanted insect or mite infestation and/or for regulating the growth of plants, where the composition is caused to act on the respective pests, their habitat or the plants to be protected from the respective pest, to the soil and/or to unwanted plants and/or the crop plants and/or their habitat.

Examples of suitable crop plants are cereals, for example wheat, rye, barley, triticale, oats or rice; beet, for example sugar or fodder beet; pome fruit, stone fruit and soft fruit, for example apples, pears, plums, peaches, almonds, cherries, strawberries, raspberries, currants or goose-berries; legumes, for example beans, lentils, peas, lucerne or soybeans; oil crops, for example oilseed rape, mustard, olives, sunflowers, coconut, cacao, castor beans, oil palm, peanuts or soybeans; cucurbits, for example pumpkins/squash, cucumbers or melons; fiber crops, for example cotton, flax, hemp or jute; citrus fruit, for example oranges, lemons, grapefruit or tangerines; vegetable plants, for example spinach, lettuce, asparagus, cabbages, carrots, onions, tomatoes, potatoes, pumpkin/squash or capiscums; plants of the laurel family, for example avocados, cinnamon or camphor; energy crops and industrial feedstock crops, for example maize, soybeans, wheat, oilseed rape, sugar cane or oil palm; maize; tobacco; nuts; coffee; tea; bananas; wine (dessert grapes and grapes for vinification); hops; grass, for example turf; sweetleaf (Stevia rebaudania); rubber plants; ornamentals and forest plants, for example flowers, shrubs, deciduous trees and coniferous trees, and the propagation material, for example seeds, and the harvested produce of these plants.

The term crop plants also includes those plants which have been modified by breeding, mutagenesis or recombinant methods, including the biotechnological agricultural products which are on the market or in the process of being developed. Genetically modified plants are plants whose genetic material has been modified in a manner which does not occur under natural conditions by hybridizing, mutations or natural recombination (i.e., recombination of the genetic material). Here, one or more genes will, as a rule, be integrated into the genetic material of the plant in order to improve the plant's properties. Such recombinant modifications also comprise posttranslational modifications of proteins, oligo- or polypeptides, for example by means of glycosylation or binding of polymers such as, for example, prenylated or farnesylated residues or PEG residues.

The invention further provides a plant propagation material, such as seed, comprising the composition of the invention. Plant propagation materials may be treated preventively together with or even before sowing, or together with or even before transplanting, with the composition of the invention. These compositions may be applied neat or, preferably, diluted to the propagation materials, more particularly seed. In the case of dilution, the composition in question may be diluted 2 to 10 times, and so the compositions used for dressing comprise 0.01% to 60% by weight, preferably 0.1% to 40% by weight, of active ingredient. Application may take place before or during sowing. The treatment of plant propagation material, more particularly the treatment of seed, is known to the skilled person, and is accomplished by dusting, coating, pelletizing, dipping or soaking the plant propagation material, with treatment taking place preferably by pelletizing, coating and dusting or by in-furrow treatment, so that, for example, premature germination of the seed is prevented. For the treatment of seed it is preferred to use suspensions. Such compositions comprise typically 1 to 800 g/l active ingredient, 1 to 200 g/l surfactants, 0 to 200 g/l antifreeze agents, 0 to 400 g/l binders, 0 to 200 g/l colorants, and solvents, preferably water.

Advantages of the invention are that the pesticides are very well stabilized in the composition. They crystallize only very slowly. Even at low temperatures there is virtually no crystallization of the pesticides. Even after dilution with water, for producing the tank mix, the pesticides show virtually no crystallization. The composition allows a high concentration of copolymer, this being advantageous in order to retard crystallization. The composition also permits a high concentration of pesticides. The copolymer may be nearly free of acidic groups, especially sulfonic acid groups, which tend to degrade various pesticide. The composition results in a high rain fastness and/or retention of the pesticide.

Examples below illustrate the invention without restricting it.

EXAMPLES

Adjuvant A: Fatty alcohol alkoxylate, water soluble, surface tension (1 g/l, 23° C.) 28-31 mN/m, viscosity (Brookfield, 23° C.) 125-145 mPas.

Adjuvant B: Fatty alcohol alkoxylate, water soluble, surface tension (1 g/l, 23° C.) 27-29 mN/m, viscosity (Brookfield, 23° C.) 70-85 mPas.

Adjuvant C: Fatty alcohol alkoxylate, water soluble, surface tension (1 g/l, 23° C.) 30-32 mN/m, viscosity (Brookfield, 23° C.) 90-100 mPas.

Diester: 1,2-Cyclohexandicarbonsäurediisononylester

Surfactant A: Nonionic triarylphenolethoxylate, HLB 12-14.

Surfactant B: Anionic alkylbenzolsulfonate, 40 wt % in aromatic solvent.

Hydrocarbons: Technical mixture of aromatic hydrocarbons, boiling range 240-300° C.

Preparation of Copolymer A (44 MMA/36 EO-MA/20 MAA)

Feed 1: 180 g of 25 wt % $C_{16-18}$-alkyl-$(EO)_{25}$-methacrylate ("EO-MA") in methyl methacrylate ("MMA")

120 g of 50 wt % $C_{16-18}$-$(EO)_{25}$-methacrylate in methacrylic acid ("MAA")

400 g isopropanol

Feed 2: 66 g isopropanol 6 g tert.-butylperpivalate 4.55 g 2-mercapto-1,2-propandiol Feed 3: 30 g isopropanol 4 g tert.-Butylperpivalate A mixture of 225 g isopropanol with 119 g of feed 1 was heated to 75° C. under stirring and aerated with nitrogen. 7.05 g of feed 2 was added. Afterwards, the remainder of feed 1 was added over 3 hours, and the remainder of feed 2 was added over 4 hours. The reaction mixture was post-polymerized. After addition of feed 3, the reaction mixture was further post-polymerized for 2 hours at 80° C. The reaction mixture was cooled down to room temperature, neutralized with 13.8 g 2-amino-2-methylpropanol (AMP) and diluted with 300 g water. Finally, isopropanol was removed under vacuum. After freeze-drying the dispersion a white powder was obtained. Copolymer A contained 44 wt % MMA, 36 wt % EO-MA, and 20 wt % MAA.

Preparation of Copolymer B (60 MMA/30 EO-MA/10 MAA)

Copolymer B contained 60 wt % MMA, 30 wt % EO-MA, and 10 wt % MAA and was prepared as described for Copolymer A above.

Example 1

Formulation of Epoxiconazol and Metconazol

The formulations A to G were prepared by mixing the components as listed in Table 1 yielding an emulsifiable concentrate (EC) of the pesticide.

TABLE 1

Composition of formulations (all amounts in wt %)

| | A | B | C | D | E | F[a] | G[a] |
|---|---|---|---|---|---|---|---|
| Epoxiconazol | 5.7 | 5.7 | 5.7 | 5.7 | 5.7 | 5.7 | 5.7 |
| Metconazol | 4.3 | 4.3 | 4.3 | 4.3 | 4.3 | 4.3 | 4.3 |
| N,N-Di-methyldodecanamide | 30 | 10 | 10 | 10 | 10 | 35 | 10 |
| 2-Ethylhexyllactate | 30 | 45 | 45 | 45 | 45 | 35 | 45 |
| Diester | — | 15 | 15 | 15 | 15 | — | 15 |
| Adjuvant A | — | — | — | 10 | 10 | — | 10 |
| Adjuvant C | 10 | 10 | 10 | — | — | 10 | — |
| Copolymer A | — | — | 10 | — | 10 | — | — |
| Copolymer B | 10 | 10 | — | 10 | — | — | — |
| Surfactant A | — | — | — | — | — | 8 | 8 |
| Surfactant B | — | — | — | — | — | 2 | 2 |

[a] Not according to the invention

Example 2

Formulation of Boscalid

The formulations A to C were prepared by mixing the components as listed in Table 2 yielding an emulsifiable concentrate (EC) of the pesticide.

TABLE 2

Composition of formulations (all amounts in wt %)

| | A | B | C[a] |
|---|---|---|---|
| Boscalid | 8 | 8 | 8 |
| N,N-Dimethyldodecanamide | 50 | 50 | 50 |
| Dibutyladipate | 22 | 22 | 22 |
| Adjuvant A | 8 | 8 | 10 |
| Adjuvant B | 2 | 2 | — |
| Copolymer A | — | 10 | — |
| Copolymer B | 10 | — | — |
| Surfactant A | — | — | 8 |
| Surfactant B | — | — | 2 |

[a] Not according to the invention

Example 3

Formulation of Fluxapyroxad

The formulations A to C were prepared by mixing the components as listed in Table 3 yielding an emulsifiable concentrate (EC) of the pesticide.

TABLE 3

Composition of formulations (all amounts in wt %)

| | A | B | C[a] |
|---|---|---|---|
| Fluxapyroxad | 9 | 9 | 9 |
| N,N-Dimethyldodecanamide | 36 | 36 | 36 |
| Diester | 35 | 35 | 35 |
| Adjuvant A | 8 | 8 | 8 |
| Adjuvant B | 2 | 2 | 2 |
| Copolymer A | — | 10 | — |
| Copolymer B | 10 | — | — |
| Surfactant A | — | — | 8 |
| Surfactant B | — | — | 2 |

[a] Not according to the invention

Example 4

Formulation of Fluxapyroxad and Difenoconazole

The formulations A to F were prepared by mixing the components as listed in Table 4 yielding an emulsifiable concentrate (EC) of the pesticide.

TABLE 4

Composition of formulations (all amounts in wt %)

| | A | B | C[a] | D | E | F[a] |
|---|---|---|---|---|---|---|
| Fluxapyroxad | 9 | 9 | 9 | 9 | 9 | 9 |
| Difenoconazole | 9 | 9 | 9 | 9 | 9 | 9 |
| N,N-Dimethyldodecanamide | 45 | 45 | 45 | 45 | 45 | 45 |
| Dibutyladipate | 10 | 10 | 10 | — | — | — |
| Hydrocarbons | — | — | — | 10 | 10 | 10 |
| Adjuvant A | 15 | 15 | 15 | 15 | 15 | 15 |
| Adjuvant B | 2 | 2 | 2 | 2 | 2 | 2 |
| Copolymer A | 10 | — | — | 10 | — | — |
| Copolymer B | — | 10 | — | — | 10 | — |
| Surfactant A | — | — | 8 | — | — | 8 |
| Surfactant B | — | — | 2 | — | — | 2 |

[a] Not according to the invention

Example 5

Storage Stability

Samples of the EC formulations of Examples 1-4 were stored at −5° C. for seven days and then viusally inspected. Table 5 summarized, if the samples stayed clear ("Clear"), or if the pesticides formed some form of precipitation ("Precipit.").

TABLE 5

A. Results of Storage Stability

| | A | B | C | D | E | F[a] | G[a] |
|---|---|---|---|---|---|---|---|
| Example 1 | Clear | Clear | Clear | Clear | Clear | Precipit. | Precipit. |

B. Results of Storage Stability

| | A | B | C[a] |
|---|---|---|---|
| Example 2 | Clear | Clear | Precipit. |
| Example 3 | Clear | Clear | Precipit. |

C. Results of Storage Stability

| | A | B | C[a] | D | E | F[a] |
|---|---|---|---|---|---|---|
| Example 3 | Clear | Clear | Precipit. | Clear | Clear | Precipit. |

[a] Not according to the invention

Example 6

Stability of the Diluted Samples in the Spray Tank

The test below was used to investigate whether the emulsifiable concentrates, following dilution to a sprayable concentration, can be used in standard sprayers without clogging the filters of the spraying machine or the spraying nozzles.

The test machine was a hydraulic sprayer with a 195 l tank, a four-piston membrane pump (at 3 bar pressure) and a spraying lance with 6 standard nozzles (type: LU 90-03). Nozzle filters used were four mesh filters (25, 50, 60, and 80 mesh), a 60-mesh mesh filter with integrated seal, and a 25-mesh slot filter. The suction filter and the pressure filter were each 50-mesh mesh filters.

The tank was first filled with 75 l of water and thereafter the 3 l of an emulsifiable concentrate (Examples 1 to 4). The mixture was mixed with a piston pump (stirring intensity: about 45 l/min) and subsequently the tank was filled up with a further 75 l of water. After pumped circulation for 15 minutes (stirring intensity: about 45 l/min) of the product mixture, the spray solution was sprayed out of the tank through the nozzles. During the test, the temperature of the spray mixture in the tank was kept constant at between 5 and 10° C. in order to simulate cold well water. The delivery test was repeated 3 times without cleaning the instruments between each application. At the end of this procedure, the filters ahead of and downstream of the pump (suction filter and pressure filter) and the filters in the nozzles (nozzle filters) were examined for residues. Table 7 summarizes the results. In the table, "clogged" means that at least one of the filters (suction, pressure or nozzle filters) showed significant fouling, causing a reduction in flow or clogging. "Free" in the table means that no significant fouling was found, and "-" means that the sample was not tested because the active(s) was not soluble in the reference solution when the polymer is not used.

TABLE 6

A

|  | A | B | C | D | E |
|---|---|---|---|---|---|
| Example 1 | Free | Free | Free | Free | Free |

B:

|  | A | B | C $^{a)}$ |
|---|---|---|---|
| Example 2 | Free | Free | — |
| Example 3 | Free | Free | Clogged |

C:

|  | A | B | C $^{a)}$ | D | E | F $^{a)}$ |
|---|---|---|---|---|---|---|
| Example 3 | Free | Free | Clogged | Free | Free | Clogged |

$^{a)}$ Not according to the invention

The invention claimed is:

1. A composition comprising a pesticide and a copolymer, wherein the copolymer contains in polymerized form
    3 to 40 wt % of acrylic acid and/or methacrylic acid (monomer A);
    10 to 45 wt % of a mono $C_{12}$-$C_{22}$ alkyl terminated poly($C_{2-6}$ alkylene glycol) (meth)acrylate (monomer B);
    20 to 80 wt % of a $C_1$-$C_8$ alkyl(meth)acrylate (monomer C); and
    up to 15 wt % further monomers D wherein D is an ethylenically unsaturated monomer;
    wherein the sum of monomers A, B, C and D equals 100%,
    wherein the sum of monomers B and C is at least 50 wt %, based on the total amount of monomers,
    wherein the pesticide is a water-insoluble pesticide which has a solubility in water of up to and including 10 g/l at 20° C., and
    wherein the composition contains up to 10 wt % water.

2. The composition according to claim 1, wherein the sum of monomers B and C is at least 60 wt %, based on the total amount of monomers.

3. The composition according to claim 1, wherein the copolymer contains
    5 to 30 wt % monomer A,
    20 to 40 wt % monomer B, and
    30 to 70 wt % monomer C, and
    up to 10 wt % further monomers D,
    wherein the sum of monomers A, B, C and D equals 100%.

4. The composition according to claim 1, wherein monomer A is methacrylic acid.

5. The composition according to claim 1, wherein monomer B is a mono $C_{14-20}$ alkyl terminated poly(ethylene glycol) (meth)acrylate.

6. The composition according to claim 1, wherein monomer C is methyl methacrylate.

7. The composition according to claim 1, wherein the weight ratio of the copolymer to the pesticide is situated in the range from 10:1 to 1:10.

8. The composition according to claim 1, wherein the copolymer is obtainable by free-radical polymerization of the monomers A-D either (i) in a solvent mixture composed of water and at least one organic solvent having a boiling point<140° C. or (ii) in one or more pure alcohols.

9. The composition according to claim 1, comprising at least 20% by weight of an organic solvent.

10. The composition according to claim 1, comprising from 30 to 95 wt % of an organic solvent, which contains at least one amide of the formula (I)

$$R^1\text{—C(O)N}(R^2)_2 \qquad (I)$$

where $R^1$ is $C_5$-$C_{19}$-alkyl, and $R^2$ is $C_1$-$C_4$-alkyl, and optionally a further solvent selected from alkyl alkanoate and hydrocarbon oil.

11. The composition according to claim 1, wherein the pesticide is present in dissolved form.

12. The composition according to claim 1 comprising
    2-20% by weight of copolymer;
    40-95% by weight of organic solvent;
    not more than 3 wt % by weight of water;
    1-25% by weight of the water-insoluble pesticide; and
    3-50% by weight of nonionic surfactant.

* * * * *